US00PP32905P2

(12) United States Plant Patent
Olesen

(10) Patent No.: US PP32,905 P2
(45) Date of Patent: Mar. 23, 2021

(54) ROSE PLANT NAMED 'POULPAH105'

(50) Latin Name: *Rosa hybrida*
Varietal Denomination: Poulpah105

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/873,980

(22) Filed: Sep. 3, 2020

(51) Int. Cl.
*A01H 6/74* (2018.01)
*A01H 5/02* (2018.01)

(52) U.S. Cl.
USPC ..... Plt./116

(58) Field of Classification Search
USPC ..... Plt./116
See application file for complete search history.

(56) References Cited

PUBLICATIONS

PLUTO Plant Variety Database Nov. 4, 2020. p. 1.*

* cited by examiner

*Primary Examiner* — Annette H Para

(57) ABSTRACT

A new garden rose plant of the miniature class which has abundant, red-pink and white striped flowers and attractive foliage. This new and distinct variety has shown to be uniform and stable in the resulting generations from asexual propagation.

1 Drawing Sheet

Botanical designation: *Rosa hybrida.*
Variety denomination: 'Poulpah105'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2012 and the resulting seeds were planted in a controlled environment in Fredensborg, Denmark. The new variety, named 'Poulpah105', originated as a single seedling from the stated cross.

The new variety may be distinguished from its male pollen parent and female seed parent primarily by the following characteristics. The male pollen parent plant has red flowers while the new variety has red-pink and white striped flowers. The female seed parent plant has near white flowers while the new variety has red and white striped flowers.

The objective of the hybridization of this rose variety was to create a new and distinct variety with unique qualities, such as:

1. Uniform and abundant red-pink and white striped flowers;
2. Vigorous, but compact growth when propagated on its own roots;
3. Exceptional disease resistance.

This combination of qualities is not present in previously available commercial cultivars of this type, known to the inventor, and distinguish 'Poulpah105' from all other varieties of which we are aware.

As part of the rose development program, Mogens N. Olesen germinated the seeds from the aforementioned hybridization during winter of 2012 and conducted evaluations on the resulting seedlings in a controlled environment in Fredensborg, Denmark. 'Poulpah105' was selected in the spring of 2013 by the inventor as a single plant from the progeny of the aforementioned hybridization.

Asexual reproduction of 'Poulpah105' by rooted cuttings was first done by Mogens N. Olesen in the nursery in Fredensborg, Denmark in July, 2013. This initial and other subsequent asexual propagations conducted in controlled environments have demonstrated that the characteristics of 'Poulpah105' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah105'. Specifically illustrated in the drawing are open flowers viewed from the side and above, flower petals and sepals detached revealing reproductive flower parts and receptacle, bare stems, mature and juvenile leaves, and a cluster of flower buds. Plants shown are 4 months of age.

DETAILED DESCRIPTION OF THE VARIETY

The following is a description of 'Poulpah105', as observed in its growth in a controlled environment greenhouse in Odense Denmark. Observed plants are 4 months old and were grown on their own roots in 19 cm containers. Color references are made using The Royal Horticultural Society (London, England) Colour Chart, 2001, except where common terms of color are used.

For a comparison, several physical characteristics of the rose variety 'Poulty019', U.S. Plant Pat. No. 26,051 are compared to 'Poulpah105' in Chart 1.

CHART 1

| | 'Poulpah105' | 'Poulty019' |
|---|---|---|
| Petal Count | 40 | 25 |
| Flower Diameter | 70 mm | 40 mm |
| General Tonality of Flower Color | Red-Purple Group N57A and White 155A. | Red Group 46A splashed with White Group N155B & Red 49A |

FLOWER AND FLOWER BUD

Blooming habit: Continuous.

Flower bud:

*Size.*—Upon opening, 22 mm in length from base of receptacle to end of bud. Bud diameter is 14 mm.

*Bud form.*—Ovoid, with a broad base.

*Bud color.*—As sepals divide petals are Red-Purple Group N57A and Red-Purple Group 59B.

*Sepal inner surface.*—Color: Yellow-Green Group 146D. Surface: Lightly pubescent.

*Sepal outer surface.*—Color: Yellow-Green Group 144A with intonations of Greyed-Orange Group 176A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—26 mm long, 10 mm wide.

*Receptacle.*—Texture: Smooth. Size: 5 mm in height, 7 mm wide. Color: Yellow-Green Group 144A. Shape: Campanulate.

*Pedicel.*—Surface: Somewhat rough with stipitate glands. Length: 32 mm. Diameter: 3 mm on average. Color: Yellow-Green Group 144B with strong intonations of Greyed-Purple Group 183B. Strength: Strong.

Flower bud development: Flower buds are borne in clusters of 3 to 5 flower buds per stem.

Flower bloom:

*Fragrance.*—Moderate floral scent.

*Duration.*—The blooms have a duration on the plant of approximately 19 days. Petals fall cleanly away from plant after flowers have fully matured.

*Size.*—Flower diameter is 70 mm when open. Flower depth is 29 mm.

*Flower shape.*—High centered double with a high pointed center which is tightly closed.

*Shape of flower, side view.*—The upper portion is flat convex. The lower portion is flattened concave.

Petalage: Under normal conditions, flowers have about 40 petals.

General tonality of flower: Open flowers are Red-Purple Group N57A and White 155A.

Petal color:

*Outer petals.*—Upper surface: White Group 155A with streaks of Red-Purple Group N57A. Lower surface: White Group 155B with streaks of Red-Purple Group N57C and Red Group 53C.

*Inner petals.*—Upper surface: At the basal zone, Yellow Group 4C. White Group 155A with streaks of Red-Purple Group N66A. Lower surface: White Group 155A with streaks of Red-Purple Group N66C.

*Basal petal spots.*—Upper surface: Yellow Group 4C. Lower surface: None.

Petals:

*Petal reflex.*—Partially reflexed.

*Margin.*—Entire and uniform. Moderate undulations.

*Shape.*—Round. Apex shape: Rounded. Base shape: Obtuse.

*Size.*—35 mm (l)×35 mm (w).

*Texture.*—Smooth.

*Thickness.*—Average.

Petaloids:

*Size.*—13 mm (l) by 8 mm (w).

*Quantity.*—5 to 7.

*Shape.*—Elliptical with an acute base and acute apex.

*Color.*—The upper side is White Group 155A with streaks of Red-Purple Group N66A. The lower surface is White Group 155A with streaks of Red-Purple Group N66C. At the petaloid base Yellow Group 4C.

Reproductive flower parts:

*Pollen.*—None observed.

*Anthers.*—Size: 2 mm in length. Color: Orange Group 24D. Quantity: 37 on average.

*Filaments.*—Color: Yellow Group 4A. Length: 3 mm.

*Pistils.*—Length: 8 mm. Quantity: 25 on average.

*Stigmas.*—Color: Greyed-Yellow Group 160D.

*Styles.*—Color: Green-White Group 157B.

*Location of stigmas.*—Superior in location relative to the length of the filaments and the height of the anthers.

*Hips.*—None Observed.

PLANT

Plant growth: Upright, bushy. Plants are 40 cm in height, and 30 cm wide.

Stems:

*Color of juvenile growth.*—Yellow-Green Group 144B with intonations of Greyed-Orange Group 176A.

*Color of mature growth.*—Yellow-Green Group 144A with strong intonations of Greyed-Orange Group 176A.

*Length.*—Canes are about 13 cm from the base of the plant to the flowering portion.

*Diameter.*—About 6 mm.

*Internodes.*—On mature canes about 44 mm between nodes.

*Surface texture.*—Young wood: Smooth. Older wood: Smooth.

Long prickles:

*Incidence.*—5 prickles per 10 cm of stem.

*Size.*—Average length of prickles on mature stems is 7 mm.

*Shape.*—Upper portion is linear. Lower portion is concave.

*Color.*—Juvenile prickles: Greyed-Purple Group 183A. Mature prickles: Greyed-Purple Group 183A.

Plant foliage:

*Compound leaf.*—110 mm (l)×65 mm (w).

*Quantity.*—2 leaves per 10 cm of stem on average.

*Leaf bearing angle to the stem.*—45 degrees.

*Color of juvenile foliage*.—Upper side: Yellow-Green Group 144A with intonations of Greyed-Orange Group 166A. Lower side: Yellow-Green Group 144B with intonations of Greyed-Purple Group 183A.

*Color of mature foliage*.—Upper side: Yellow-Green Group 147A. Lower side: Yellow-Green Group 146B.

Plant leaves and leaflets:

*Stipules*.—Size: 11 mm long, mm wide. Quantity: 2 per compound leaf. Shape: Linear, slightly broad based with outward extending apices. Margins: Finely serrated. Color: Greyed-Purple Group 183A and Yellow-Green Group 144A.

*Petiole*.—Length: 20 mm. Diameter: 2 mm. Upper surface color: Yellow-Green Group 144A with intonations of Greyed-Purple Group 183B. Lower surface color: Yellow-Green Group 144A.

*Rachis*.—Length: 30 mm. Upper surface color: Yellow-Green Group 144A with intonations of Greyed-Purple Group 183B. Lower surface color: Yellow-Green Group 144A.

*Leaflet*.—Quantity: Normally 5 leaflets. Margins: Serrated. Size: Terminal leaflets are about 50 mm long, 50 mm wide. Shape: Generally round. Base: Rounded. Apex: Round with slight point. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah105', substantially as illustrated and described herein, due to its abundant red-pink and white striped flowers, disease resistance, and extended period of bloom.

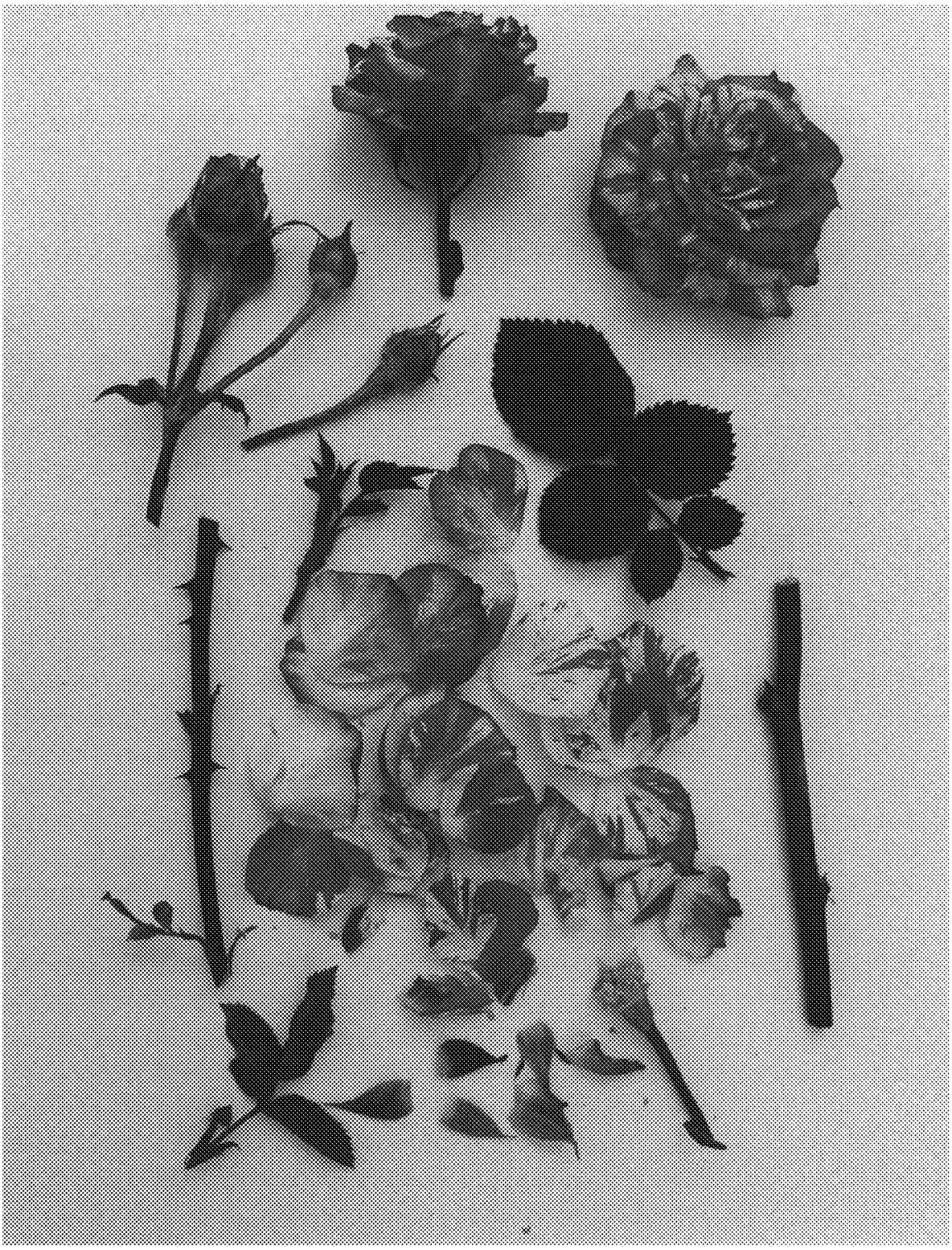

* * * * *